United States Patent [19]

Heimlich et al.

[11] 4,431,854

[45] Feb. 14, 1984

[54] CONTINUOUS PREPARATION OF ETHYLBENZENE IN A HETEROGENEOUS-PHASE REACTION

[75] Inventors: Guenther Heimlich, Ainring; Gregor Tremmel, Gruenstadt; Manfred Lieb, Ludwigshafen, all of Fed. Rep. of Germany

[73] Assignee: BASF Aktiengesellschaft, Fed. Rep. of Germany

[21] Appl. No.: 305,848

[22] Filed: Sep. 25, 1981

[30] Foreign Application Priority Data

Oct. 22, 1980 [DE] Fed. Rep. of Germany ....... 3039760

[51] Int. Cl.³ .............................................. C07C 2/70
[52] U.S. Cl. .................................... 585/313; 585/323; 585/461
[58] Field of Search ................... 585/461, 323, 313

[56] References Cited

U.S. PATENT DOCUMENTS

| | | | |
|---|---|---|---|
| 3,448,161 | 6/1969 | Garcia et al. | 585/461 |
| 3,536,772 | 10/1970 | Csomontanyi et al. | 585/313 |
| 3,551,510 | 12/1970 | Pollitzer et al. | 585/323 |
| 3,751,504 | 8/1973 | Keown et al. | 585/323 |
| 3,848,012 | 11/1974 | Applegath et al. | 585/449 |
| 4,169,111 | 9/1979 | Wight | 585/323 |
| 4,179,473 | 12/1979 | Cox | 585/313 |

FOREIGN PATENT DOCUMENTS 639873  7/1950  United Kingdom .

*Primary Examiner*—Curtis R. Davis
*Attorney, Agent, or Firm*—Keil & Witherspoon

[57] ABSTRACT

A process for the continuous preparation of ethylbenzene in a heterogeneous-phase reaction by alkylating benzene with ethylene in the presence of a catalyst based on a complex organic aluminum chloride compound and a co-catalyst at an elevated temperature and elevated pressure, with a residence time of from 5 to 60 minutes in one or more reaction zones, the reaction mixture, after completion of the reaction, being fed into a pressure vessel and vigorously mixed therein for from 20 to 60 minutes at from 120° to 160° C.

3 Claims, No Drawings

CONTINUOUS PREPARATION OF ETHYLBENZENE IN A HETEROGENEOUS-PHASE REACTION

The present invention relates to a process for the continuous preparation of ethylbenzene in a heterogeneous-phase reaction, by alkylating benzene with ethylene, using a Friedel-Crafts catalyst, separating the reaction mixture into two phases, working up the less dense phase so as to isolate the useful product, and recycling the remainder of the less dense phase, together with the denser phase, to the reaction zone.

The reaction of benzene with ethylene in the presense of a Friedel-Crafts catalyst to give ethylbenzene is one of a number of processes which is extensively employed in industry. Details of the various processes employed industrially are given in the following publications:

(1) Kunststoff-Handbuch, Volume V, Polystyrene, Carl Hanser-Verlag (1969), pages 18–23
(2) U.S. Pat. No. 3,448,161
(3) U.S. Pat. No. 3,848,012
(4) U.S. Pat. No. 3,751,504
(5) Ullmann, Enzyklopädie der techn. Chemie, Volume 14, 4th edition, 1977, pages 673 et seq.

The preparation of ethylbenzene by alkylating benzene with ethylene in the presence of a Friedel-Crafts catalyst and of a promoter for the latter as a rule gives a reaction mixture which in addition to the useful product, namely ethylbenzene, contains unconverted benzene together with diethylbenzene, triethylbenzene and high-boiling polyethylbenzenes. Both the benzene and the polyethylated benzenes are, in industrial operation, separated from the ethylbenzene by distillation and fed to the alkylation reactor. In the presence of excess benzene, ethylbenzene is formed from the polyethylbenzenes by disproportionation under the reaction conditions employed. In this way, a yield of ethylbenzene of $\geq 98\%$, based on benzene, is achieved.

In order to minimize energy costs, the synthesis of ethylbenzene is carried out at optimum conversion while limiting the amount of benzene employed. In the conventional process, where ethylation and transethylation take place in the same reaction zone, at up to 130° C., at most 2.0 to about 3 moles of benzene are employed per mole of ethylene. If the benzene/ethylene ratio is reduced to below 2.0:1, the polyethylbenzene content increases disproportionately and at the same time the concentration of benzene and ethylbenzene in the material leaving the reactor decreases. This, then, is one of the obstacles to reducing the cost of synthesis of ethylbenzene.

Another method of improving the conversion is to increase the reaction temperature from 130° C. to $\leq 160°$ C. This process again is subject to limits. It is true that the ethylbenzene concentration rises, but so, at the same time, does the polyethylbenzene content, so that the benzene concentration correspondingly decreases.

Attempts to increase the conversion by using larger amounts of catalyst or co-catalyst have failed.

It is an object of the present invention to overcome the above disadvantages in the conventional processes.

We have found that this object is achieved by the measures set forth in the claims.

The process for the continuous preparation of ethylbenzene by a heterogeneous-phase reaction is sufficiently well known, for example from (1), (3) or (5), so that in the text which follows it need only be discussed briefly as far as the features of the preamble of the claim are concerned.

To carry out the process according to the invention, benzene is reacted with ethylene in a molar ratio of benzene to ethylene of from 1.5 to 3.4:1. The catalyst used is a conventional Friedel-Crafts catalyst, preferably aluminum chloride. The catalyst is introduced into the reaction zone in the form of a solution, in a conventional manner; the solvent used in this solution can be a by-product of the reaction, especially diethylbenzene. The amount of catalyst consumed in the synthesis is replaced by adding from 0.001 to 0.0005 of dry aluminum chloride, $AlCl_3$, per mole of benzene. As a rule, a co-catalyst, namely an anhydrous hydrogen halide, preferably hydrogen chloride, is also used, in a conventional amount familiar to the skilled worker. The reaction is carried out at from 100° to 160° C., preferably from 120° to 150° C., at a pressure of from 0.005 to 5 bar. The residence time in the reaction zone can be from 5 to 60 minutes, especially from 10 to 40 minutes. The process according to the invention is usually carried out in one reaction zone. If a plurality of reaction zones is employed, they are preferably arranged in series. The material leaving the reaction zone is separated in a conventional manner in a horizontal vessel, after appropriate cooling, into a less dense organic phase (a) and a denser organic phase (b) which consists essentially of the complex organic aluminum chloride compounds. The denser organic phase (b) is recycled to the reaction zone. The less dense organic phase (a), commonly referred to as crude ethylbenzene mixture, consists essentially of the useful product as well as unconverted benzene, higher ethylbenzenes and residues, some being of unknown nature. This phase is worked up by fractional distillation, with isolation of the useful product. The other products which are obtained, on fractional distillation, in the various columns, namely the benzene column, the ethylbenzene column and/or the polyethylbenzene column, are recycled to the reaction zone. If desired, a proportion of the residue from the polyethylbenzene column can also be recycled (for details, compare German Patent Application P No. 30 09 932.3). Conventional processes, for example washing with sodium hydroxide solution and the like, are employed to remove residual aluminum chloride from the less dense organic phase.

The denser organic phase, which consists essentially of the complex organic aluminum chloride compounds, is taken off the horizontal vessel and pumped back to the reactor. For re-use of the denser organic phase at temperatures of 130°–160° C. in the reaction zone, it is essential that anhydrous benzene should be employed and that the separation of the denser organic phase in the horizontal vessel should take place at below 40° C. Provided these preconditions are met, the catalytic activity of the recycled complex organic aluminum chloride compounds is unimpaired, even at reaction temperatures above 130° C. It is essential, in carrying out the process according to the invention, that the material leaving the reaction zone, or leaving the last reaction zone, should, before phase separation, be introduced into a pressure vessel and vigorously mixed therein. The pressure reactor used to receive the reaction mixture can be of any desired construction and can include devices for vigorous mixing of the reaction mixture. For example, it can be a stirred reactor which provides vigorous radial mixing. Mixing can also be effected by taking some of the mixture from the pressure reactor which is located downstream of the reaction zone and recycling part of the contents to this pressure reactor by pumping. What is essential under all circumstances is to provide vigorous mixing, ie. to set up an equilibrium sufficiently rapidly. The inner lining of this pressure reactor must, like the lining of the reaction zone itself, be stable to the Lewis acid employed. The treatment in the pressure vessel can be carried out at from 40° C. to 160° C. For energetic and kinetic reasons, it is however preferably carried out only slightly below the temperature of the reaction zone, ie. essentially at from 120° to 150° C. Under the above conditions, equilibrium is set up relatively rapidly and without damage to the catalyst. The residence time of the material in the pressure vessel should be not less than 20 minutes and it can be up to 40 minutes. The design of this pressure vessel is substantially at the discretion of the skilled worker; at low temperatures, equilibrium is set up more slowly, and accordingly vessels of larger volume have to be used. Within the stated temperature range of 120°–150° C., a thermodynamic equilibrium is set up, at a rate depending on the particular temperature, and the composition of the crude ethylbenzene shifts in favor of an increase in ethylbenzene content. According to our results, approximately the following equilibrium is set up in the pressure vessel:

| Material | Content in % by weight |
|---|---|
| Unknown products: | 1.5 |
| Benzene: | 39.0 |
| Ethylbenzene: | 46.0 |
| Polyethylbenzene: | 13.5 |

We assume that the equilibrium is set up as a result of an exchange reaction between aromatics in the organic aluminum chloride complex and the crude ethylbenzene. Accordingly, after completion of the treatment in the pressure vessel, the ligand composition of the catalyst corresponds to the composition of the crude ethylbenzene.

In contrast to the prior art process for the synthesis of ethylbenzene by a heterogeneous-phase reaction, the novel process can also be carried out above 130° C. Even though this causes an increase in the concentration of polyethylbenzenes in the reaction zone, the after-treatment according to the invention, in the pressure vessel, results in the higher concentration of ethylbenzene shown above. The novel process is also more flexible than the prior art processes, since it is also possible to use less than 2 moles of benzene per mole of ethylene without reducing the yield of ethylbenzene. The consumption of aluminum chloride is also low in the process according to the invention, being from 0.1 to 0.15 mole percent per mole of ethylbenzene. The transfer of the contents of the reaction zone into the pressure vessel can, if desired, be accompanied by a drop in pressure. It is also possible to feed co-catalyst into the pressure vessel. If the above pressure reduction is employed, the pressure vessel is brought 0.5–2 bar below the pressure employed in the reaction zone.

The Examples which follow illustrate the invention. Percentages are by weight, unless stated otherwise.

EXAMPLE 1

The experiments for determining the setting-up of the equilibrium were carried out in a laboratory apparatus. 2,000 g of material were taken from an industrial reactor, in which the synthesis of ethylbenzene was carried out continuously by heterogeneous-phase reaction in a zone at 135° C., and were stirred vigorously in a glass apparatus. Various temperatures in the range from 20° to 150° C. were chosen and the equilibrium composition was determined within this range. To maintain the temperature set up, the glass apparatus was located in a thermostated bath. Samples were taken at intervals of 20 or 30 minutes. After separating the less dense phase (crude ethylbenzene phase) from the denser phase, the crude ethylbenzene was analyzed by gas chromatography. The Table shows the results of the analyses, the crude ethylbenzene phase being taken as 100%.

EXAMPLE 2

The setting-up of the equilibrium was determined as described above, but in an industrial plant, using the actual reaction zone as the pressure reactor. For this, it was merely necessary to stop the feed of ethylene, benzene and polyethylbenzene to the reaction zone. The experiments were carried out at 135° C. The reactor contents were circulated by pumping and the change in composition of the crude ethylbenzene with time was determined. The results are shown in the Table. Comparison of the results shows that there are no differences between the laboratory results and those obtained in the industrial trial and that, as already stated, an equilibrium is set up, after a certain residence time at an elevated temperature, which corresponds to ethylbenzene contents of about 44–45.9% in the crude ethylbenzene.

TABLE

| | Temperature °C. | Mixing time in minutes | Benzene (%) | Ethyl benzene (%) | Poly-Polyethyl benzene (%) | Unknown materials (%) |
|---|---|---|---|---|---|---|
| Laboratory | 20 | 0 | 42.59 | 40.50 | 15.12 | 1.79 |
| | | 30 | 42.34 | 41.67 | 14.18 | 1.81 |
| | | 60 | 41.82 | 41.63 | 14.16 | 1.94 |
| | | 90 | 42.50 | 41.59 | 14.17 | 1.74 |
| | | 120 | 41.78 | 42.06 | 14.42 | 1.74 |
| | | 150 | 42.80 | 41.88 | 13.53 | 1.79 |
| | | 1.110 | 41.20 | 43.87 | 13.57 | 1.56 |
| | 80 | 1.170 | 39.88 | 44.88 | 13.31 | 1.93 |
| | 60 | 0 | 42.79 | 40.24 | 15.03 | 1.94 |
| | | 30 | 41.50 | 41.10 | 15.59 | 1.81 |
| | | 60 | 41.53 | 41.78 | 15.00 | 1.69 |
| | | 90 | 40.99 | 42.67 | 14.55 | 1.79 |
| | | 120 | 40.91 | 43.12 | 14.16 | 1.81 |
| | | 150 | 40.90 | 43.79 | 13.43 | 1.88 |
| | | 180 | 40.76 | 43.69 | 13.67 | 1.88 |
| | 100 | 0 | 42.01 | 40.90 | 15.24 | 1.85 |
| | | 30 | 41.65 | 42.02 | 14.61 | 1.72 |
| | | 60 | 40.74 | 42.78 | 14.74 | 1.74 |
| | | 90 | 40.29 | 43.48 | 14.32 | 1.91 |
| | | 120 | 40.24 | 44.57 | 13.40 | 1.79 |
| | 125 | 0 | 44.72 | 40.95 | 12.67 | 1.66 |
| | | 30 | 40.19 | 44.87 | 13.10 | 1.84 |
| | | 60 | 39.24 | 45.86 | 13.15 | 1.74 |
| | 150 | 0 | 42.78 | 41.84 | 13.59 | 1.79 |
| | | 20 | 39.57 | 45.12 | 13.77 | 1.54 |
| | | 40 | 37.83 | 45.31 | 15.35 | 1.61 |
| Plant operation | 135 | 0 | 44.26 | 41.20 | 12.74 | 1.80 |
| | | 30 | 40.76 | 44.83 | 12.69 | 1.72 |
| | | 60 | 40.34 | 44.64 | 13.28 | 1.74 |

We claim:

1. A process for the continuous preparation of ethylbenzene in a heterogeneous-phase reaction, by alkylating benzene with ethylene, using a molar ratio of benzene to ethylene of from 1.5 to 3.4:1, in the presence of a catalyst based on a complex organic aluminum chloride compound and used in an amount of from 0.06 to 0.02 mole of AlCl$_3$ per mole of benzene, and in the presence or absence of a conventional amount of an anhydrous hydrogen halide as co-catalyst, at from 130° to 160° C. and under a pressure of from 2 to 5 bar, using a residence time of from 5 to 60 minutes and carrying out the reaction in at least one zone, the material discharged from the zone being separated into (a) a less dense organic phase, which consists essentially of the useful product, unconverted benzene, higher ethylbenzenes and residues, and (b) a denser organic phase which consists essentially of the complex organic aluminum chloride compound, and the less dense phase (a) being worked up by distillation, with isolation of the useful product and recycling of unconverted benzene, while the denser phase (b) is recycled to the reaction zone and losses of catalyst or co-catalyst are made up, in which process the material formed in the reaction zone is vigorously mixed in a pressure vessel before phase separation for not less than 20 minutes and up to 60 minutes at from 120° to 160° C., the pressure in the pressure vessel being either the same as the pressure in the reaction zone or is from 0.5 to 2 bar below the pressure in the reaction zone.

2. The process of claim 1, wherein the mixing treatment is carried out in a separate vessel and at a pressure that is from 0.5 to 2 bar lower than the pressure in the reaction vessel.

3. The process of claim 2 wherein the treatment in the separate vessel takes place with the addition of co-catalyst.

* * * * *